United States Patent [19]

Razavi

[11] Patent Number: 5,158,920
[45] Date of Patent: Oct. 27, 1992

[54] PROCESS FOR PRODUCING STEREOSPECIFIC POLYMERS

[75] Inventor: Abbas Razavi, Patourage, Belgium

[73] Assignee: Fina Technology, Inc., Dallas, Tex.

[21] Appl. No.: 725,702

[22] Filed: Jul. 3, 1991

Related U.S. Application Data

[63] Continuation-in-part of Ser. No. 418,886, Oct. 10, 1989, which is a continuation-in-part of Ser. No. 220,007, Jul. 15, 1988, Pat. No. 4,892,851.

[51] Int. Cl.$^5$ .............. C08F 4/64; C08F 4/68; C08F 4/69
[52] U.S. Cl. .............. 502/152; 502/103; 502/117; 556/43; 556/53; 556/58
[58] Field of Search .............. 502/117; 556/43, 53, 556/58; 502/103, 152

[56] References Cited

U.S. PATENT DOCUMENTS

| | | | |
|---|---|---|---|
| 4,794,096 | 12/1988 | Ewen | 502/117 |
| 4,892,851 | 1/1990 | Ewen et al. | 556/43 X |
| 4,975,403 | 12/1990 | Ewen | 502/117 X |

FOREIGN PATENT DOCUMENTS

| | | | |
|---|---|---|---|
| 185918 | 7/1986 | European Pat. Off. | 502/117 |
| 277003 | 8/1988 | European Pat. Off. | 502/117 |
| 277004 | 8/1988 | European Pat. Off. | 502/117 |

OTHER PUBLICATIONS

Jordan et al., JACS 1986, 108, 7410-11.
Jordan et al., JACS 1986, 108, 1718-19.
Zambelli et al., Macromolecules, 1989, 22, 2186-89.

*Primary Examiner*—Patrick P. Garvin
*Attorney, Agent, or Firm*—William D. Jackson; Jim D. Wheelington

[57] ABSTRACT

Process for the preparation of bridged metallocene catalysts. A substituted or unsubstituted cyclopentadiene is deprotonated in a polar solvent to form a solution of the corresponding anion species. The solution is then cooled to a temperature within the range of about $-10°$ to $-30°$ C. A minor amount of a solution of substituted fulvene in a polar solvent is added to a major quantity of the solution of anionic substituted or unsubstituted cyclopentadiene. The substituted fulvene is present in the solvent to provide a concentration of less than 2 molal. The substituted fulvene is disubstituted on the terminal (6) carbon atom and may be substituted or unsubstituted on the cyclopentadienyl ring. The resulting mixture is warmed to a temperature within the range of about 0° to 25° C. (room temperature) to produce a bridged cyclopentadienyl ligand. The bridged ligand is then recovered and contacted with a transition metal halide or hydrocarbon compound under reaction conditions sufficient to complex the bridged ligand to produce a bridged metallocene. In the preparation of syndiospecific metallocene catalysts one cyclopentadienyl group is a substituted or unsubstituted cyclopentadienyl ring and the other is a substituted cyclopentadienyl group sterically different from the first ring structure. Here, the cyclopentadienyl compound subjected to the protonation reaction can be a substituted or unsubstituted fluorenyl or indenyl group which is deprotonated and reacted with a 6, 6-dialkyl fulvene.

33 Claims, No Drawings

PROCESS FOR PRODUCING STEREOSPECIFIC POLYMERS

This application is a continuation-in-part of U.S. application Ser. No. 418,886, filed Oct. 10, 1989, which in turn, is a continuation-in-part of application Ser. No. 220,007 filed Jul. 15, 1988 now U.S. Pat. No. 4,892,851.

TECHNICAL FIELD

This invention relates to bridged metallocene catalysts useful in the production of stereospecific polymers from ethylenically unsaturated compounds and more particularly, to processes for preparing such catalysts by the reaction of a deprotonized substituted or unsubstituted cyclopentadiene with a substituted fulvene.

BACKGROUND OF THE INVENTION

Syndiotacticity and isotacticity are stereospecific structural relationships which may be involved in the formation of stereoregular polymers from various monomers. Stereospecific propagation may be applied in the polymerization of ethylenically unsaturated monomers such as $C_{3+}$ alpha olefins, 1-dienes such as 1,3-butadiene, substituted vinyl compounds such as vinyl aromatics, e.g., styrene or vinyl chloride, vinyl chloride, vinyl ethers such as alkyl vinyl ethers, e.g., isobutyl vinyl ether, or even aryl vinyl ethers. Stereospecific polymer propagation is probably of most significance in the production of polypropylene of isotactic or syndiotactic structure.

Syndotactic polymers have a unique stereochemical structure in which monomeric units having enantiomorphic configuration of the asymmetrical carbon atoms follow each other alternately and regularly in the main polymer chain. Syndiotactic polypropylene was first disclosed by Natta et al. in U.S. Pat. No. 3,258,455. As disclosed in this patent, syndiotactic polypropylene can be produced by using a catalyst prepared from titanium trichloride and diethylaluminum monochloride. A later patent to Natta et al., U.S. Pat. No. 3,305,538, discloses the use of vanadium triacetylacetonate or halogenated vanadium compounds in combination with organic aluminum compounds for producing syndiotactic polypropylene. U.S. Pat. No. 3,364,190 to Emrick, discloses the use of a catalyst system composed of finely divided titanium or vanadium trichloride, aluminum chloride, a trialkyl aluminum and a phosphorus-containing Lewis base in the production of syndiotactic polypropylene.

As disclosed in the aforementioned patents, and as is known in the art, the structure and properties of syndiotactic polypropylene differ significantly from those of isotactic polypropylene. The isotactic structure is typically described as having the methyl groups attached to the tertiary carbon atoms of successive monomeric units on the same side of a hypothetical plane through the main chain of the polymer, e.g., the methyl groups are all above or below the plane. Using the Fischer projection formula, the stereochemical sequence of isotactic polypropylene is described as follows:

Another way of describing the structure is through the use of NMR. Bovey's NMR nomenclature for an isotactic pentad is ... mmmm ... with each "m" representing a "meso" dyad, or successive methyl groups on the same side of the plane. As is known in the art, any deviation or inversion in the structure of the chain lowers the degree of isotacticity and crystallinity of the polymer. In contrast to the isotactic structure, syndiotactic propylene polymers are those in which the methyl groups attached to the tertiary carbon atoms of successive monomeric units in the chain lie on alternate sides of the plane of the polymer. Syndiotactic polypropylene is shown in zig-zag representation as follows:

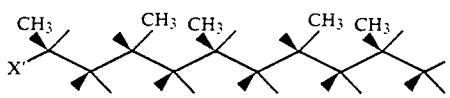

Corresponding representations for syndiotactic polyvinylchloride and polystyrene, respectively, are:

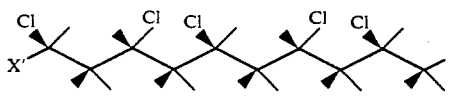

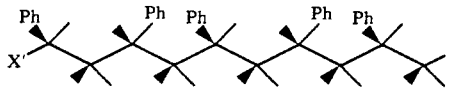

Using the Fischer projection formula, the structure of a syndiotactic polymer or polymer block for polypropylene is designated as:

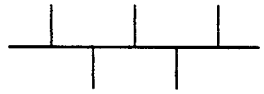

In NMR nonmenclature, this pentad is described as . . . rrrr . . . , in which each "r" represents a "racemic" dyad, i.e., successive methyl groups on alternate sides of the plane. The percentage of r dyads in the chain determines the degree of syndiotacticity of the polymer. Syndiotactic polymers are crystalline and, like the isotactic polymers, are insoluble in xylene. This crystallinity distinguishes both syndiotactic and isotactic polymers from an atactic polymer, which is soluble in xylene. An atactic polymer exhibits no regular order of repeating unit configuration in the polymer chain and forms essentially a waxy product.

While it is possible for a catalyst to produce all three types of polymers, it is desirable for a catalyst to produce predominantly isotactic or syndiotactic polymers with very little atactic polymer. Catalysts that produce isotactic polyolefins are disclosed in U.S. Pat. No. 4,794,096, issued Dec. 27, 1988 and U.S. Pat. No. 4,975,403, issued Dec. 4, 1990. These patents disclose chiral, stereorigid metallocene catalysts that polymerize olefins to form isotactic polymers and are especially useful in the polymerization of highly isotactic polypropylene.

As disclosed, for example, in the aforementioned U.S. Pat. No. 4,794,096, stereorigidity in a metallocene ligand is imparted by means of a structural bridge extending between cyclopentadienyl groups. Specifically disclosed in this patent are stereoregular hafnium metallocenes, which may be characterized by the following formula:

$$R''(C_5(R')_4)_2 HfQ_p \tag{1}$$

In formula (1), (C$_5$(R')$_4$) is a cyclopentadienyl or substituted cyclopentadienyl group, R' is independently hydrogen or a hydrocarbyl radical having 1-20 carbon atoms, and R" is a structural bridge extending between the cyclopentadienyl rings. Q is a halogen or a hydrocarbon radical, such as an alkyl, aryl, alkenyl, alkylaryl or arylalkyl, having 1-20 carbon atoms and 0<p<3.

Catalysts that produce syndiotactic polypropylene or other syndiotactic polyolefins and methods for the preparation of such catalysts are disclosed in the aforementioned U.S. Pat. No. 4,892,851. These catalysts are also bridged stereorigid metallocene catalysts, but, in this case, the catalysts have a structural bridge extending between dissimilar cyclopentadienyl groups, and may be characterized by the formula:

$$R''(C_pR_n)(C_pR'_m)MeQ_k \tag{2}$$

In formula (2), C$_p$ represents a cyclopentadienyl or substituted cyclopentadienyl ring, and R and R' represent hydrocarbyl radicals having 1-20 carbon atoms. R" is a structural bridge between the rings imparting stereorigidity to the catalyst. Me represents a transition metal, and Q a hydrocarbyl radical or halogen. R'm is selected so that (C$_p$R'$_m$) is a sterically different substituted cyclopentadienyl ring than (C$_p$R$_n$); n varies from 0 to 4 (0 designating no hydrocarbyl groups, i.e., an unsubstituted cyclopentadienyl ring), m varies from 1-4, and K is from 0-3. The sterically different cyclopentadienyl rings produce a predominantly syndiotactic polymer rather than an isotactic polymer.

Specifically disclosed in U.S. Pat. No. 4,892,851, are synthesis procedures for the preparation of bridged metallocene ligands having a dissimilar cyclopentadienyl group by the reaction of 6, 6 dimethyl fulvene with a substituted cyclopentadiene, such as fluorene, to produce a ligand characterized by an isopropylidene bridge structure. The ligand coupling reaction is carried out under relatively cold temperature conditions and is characterized by the addition of a relatively concentrated solution of the substituted fulvene to a relatively dilute solution of the fluorene, both in a polar solvent, specifically, tetrahydrofuran. After formation of the ligand, aromatization may be accomplished by the addition of n-butyl lithium.

The aforementioned parent application Ser. No. 418,886, discloses stereorigid cationic metallocenes, including, inter alia, bridged metallocene catalysts useful for the production of syndiotactic polymers. The bridged metallocene catalysts of application Ser. No. 418,886 comprise an unbalanced metallocene cation and a stable, non-coordinating counteranion for the metallocene cation. The metallocene cation is characterized by a cationic metallocene ligand having sterically dissimilar ring structures joined to a positively charged coordinating transition metal atom. The dissimilar cyclopentadienyl rings, at least one of which is substituted, are both in a stereorigid relationship relative to the coordinating metallocene of the metal atom catalyst, and, as noted previously, the stereorigid relationship may be imparted by means of a structural bridge between the dissimilar cyclopentadienyl rings.

Cationic metallocene catalysts of yet another type are disclosed in EPO Pat. Nos. 277,003 and 277,004 to Turner. As disclosed in these patents, a bis(cyclopentadienyl) zirconium, titanium, or hafnium compound is reacted with a second compound comprising a cation capable of donating a proton or an ion exchange compound comprising a cation which will irreversibly react with a ligand on the first compound, and a bulky, stable ion. The catalysts described in the European Patents Nos. 277,003 and 277,004 are disclosed as especially useful in the polymerization of ethylene, and more generally, in the polymerization of alpha olefins, diolefins and/or an acetylenically unsaturated compound containing from 2-18 carbon atoms. Stereospecificity, or lack thereof, is not generally discussed in these patents, although in 277,004, examples are given of producing atactic polypropylene, and in one instance (Example 39), isotactic polypropylene.

SUMMARY OF THE INVENTION

In accordance with the present invention, there is provided a process for the preparation of bridged metallocene catalysts. In carrying out the invention, a substituted or unsubstituted cyclopentadiene is subjected to deprotonation in a polar solvent to form the corresponding anion species. The resulting solution of the anionic species is then cooled to a temperature, which, while normally sub-zero, is substantially above the temperature employed in the synthesis procedure of U.S. Pat. No. 4,892,851. As a practical matter, the temperature need not be lower than about −30° C.; preferably, the reaction product is cooled to a temperature within the range of about −10° to −30° C.

A second reaction component is provided in the form of a solution of a substituted fulvene added in a polar solvent to provide a concentration of less than 2 molal (m). The substituted fulvene is disubstituted on the terminal (6) carbon atom and may be substituted or unsubstituted on the cyclopentadienyl ring. The substituted fulvene solution is added in minor quantities to a major quantity of the solution of anionic substituted or unsubstituted cyclopentadiene.

The temperature of the resulting mixture is warmed to a temperature within the range of about 0° to 25° C. (room temperature) to produce a bridged cyclopentadienyl ligand. The bridged ligand is then recovered and contacted with a metal compound of the formula MeQ$_k$ under reaction conditions sufficient to complex the bridged ligand to produce a bridged metallocene. The complexing procedure may be carried out by following the corresponding protocol in U.S. Pat. No. 4,892,851, but preferably, an improved procedure, as described hereinafter, is employed in the complexing step. In the formula MeQ$_k$, Me is a transition metal from group 4b, 5b, or 6b of the Periodic Table of Elements, each Q is a halogen, preferably Cl, Br or I, and most preferably, Cl, or a C$_1$-C$_{20}$ hydrocarbyl radical, and 3<k<6.

A preferred application of the present invention is in the preparation of metallocene catalysts useful in the syndiotactic propagation of polymer chains, that is, unbalanced stereorigid catalysts having sterically different cyclopentadienyl groups. More specifically, one of the cyclopentadienyl groups of the ligand structure is a substituted or unsubstituted cyclopentadienyl ring and the other is a substituted cyclopentadienyl group which is sterically different from the first ring structure. Preferably, the cyclopentadienyl compound subjected to the protonation reaction is a substituted or unsubstituted fluorenyl or a substituted or unsubstituted indenyl group. Especially preferred ligand structures can be formulated employing a fluorene or indene which is deprotonated and reacted with a 6, 6-dialkyl fulvene, which is otherwise unsubstituted.

DETAILED DESCRIPTION

The present invention involves processes for the preparation of stereospecific metallocenes which may be neutral or cationic, and which are useful in stereospecific polymer propagation, especially syndiotactic polymer propagation. The term metallocene, as used herein, and in accordance with normal art usage, denotes an organometallic coordination compound in which two cyclo-C5 ligands (cyclopentadienyl or substituted cyclopentadienyl rings) are bonded to a central or "sandwiched" metal atom which may be provided by a transition metal or metal halide, alkyl, alkoxy, or alkoxy halide or the like. Such structures are sometimes referred to as "molecular sandwiches" since the cyclo-C5 ligands are oriented above or below the plane of the central coordinated metal atom. The metallocene catalysts produced in accordance with the present invention may be neutral or they may be cationic. By the term "cationic metallocene" is meant a metallocene in which the central coordinated metal atom carries a positive charge, that is, the metallocene complex is a cation associated with a stable anion. The neutral or cationic metallocenes produced in accordance with the present invention are stereorigid by virtue of a chemical bridge extending between the cyclopentadienyl (or substituted cyclopentadienyl) rings.

As noted previously, parent U.S. Pat. No. 4,892,851 discloses the preparation of syndiotactic polypropylene or other polyolefins through the use of bridged stereorigid metallocene catalysts. Parent application Ser. No. 418,886 discloses stereorigid metallocene catalysts, including those in which stereorigidity is imparted by a bridge structure, in which a neutral metallocene is ionized to provide a stable cationic catalyst. Neutral metallocenes produced in accordance with the present invention may be converted to the cationic form following procedures of the type disclosed in the aforementioned European Patents 277,003 and 277,004, but they preferably are prepared by a process employing a triphenylcarbenium borate as discussed in greater detail in application Ser. No. 419,046, filed Oct. 30, 1989. In the bridged metallocene catalysts prepared in accordance with the present invention, the cyclopentadienyl groups may be the same if they are to be used for isotactic polymer propagation, or different if they are to be used for syndiotactic polymer propagation.

As noted previously, a preferred application of the present invention is in the preparation of syndiospecific catalysts having a stereorigid bridge structure extending between dissimilar cyclopentadienyl rings. Such syndiospecific metallocenes may be characterized by the previously described formula (2):

$$R''(C_pR_n)(C_pR'_m) \text{Me}Q_k \qquad (2)$$

In formula (2), R and R' are selected such that $C_pR'_m$ is a sterically different ring than $C_pR_n$. Isospecific catalysts prepared in accordance with the invention may be characterized by formula (2) with the proviso that the two cyclopentadienyl groups, which may be substituted or unsubstituted, are the same. That is, $C_pR'_m$ is the same as $C_pR_n$ and m and n may both vary from 0 to 4. Such isospecific catalysts are specifically characterized by the formula:

$$R''(C_pR_n)_2 \text{Me}Q_k \qquad (3)$$

The stereorigid metallocene catalysts prepared by the present invention may be neutral or cationic metallocenes. The cationic metallocenes correspond to the structures depicted by formula (2) with the exception that k is an integer from 0 to 2, rather than the transition metal being possibly trisubstituted, as in the case of the neutral metallocenes. Such cationic metallocene catalysts may be characterized by the following formula:

$$[R''C_pR_n)(C_pR'_m) \text{Me}Q_k]^+ P^- \qquad (4)$$

In formula (3), Cp, R, R', Me, m, and n, are as described previously. K is a number from 0 to 2, and P is a stable noncoordinating counter anion. The cationic catalysts of formula (4) may be prepared from the corresponding neutral metallocenes using procedures as described below.

The counter anion indicated by P in formula (4) is a compatible noncoordinating anion which may be of the type described in the aforementioned Turner European patents. The anion P either does not coordinate with the metallocene cation or is only weakly coordinated to the cation, thereby remaining sufficiently liable to be displaced by a neutral Lewis base. As described in the Turner patents, the term "compatible noncoordinating anion" identifies an anion which, when functioning as a stabilizing anion in the metallocene catalyst system, does not transfer an anionic substituent or fragment thereof to the cation to form a neutral metallocene and boron byproduct or other neutral metal or metalloid byproduct, as the case may be. Suitable noncoordinating anions include: $[W(PhF_5)]^-$, $[Mo(PhF_5)]^-$ (wherein $PhF_5$ is pentafluoryl phenyl), $[ClO_4]^-$, $[SbR_6]^-$, and $[AlR_4]^-$(wherein each R is independently, Cl, a $C_1-C_5$ alkyl group, preferably, a methyl group, an aryl group, e.g., a phenyl or substituted phenyl group, or a fluorinated aryl group. For a further description of compatible noncoordinating anions and their associated cations which may be employed in the present invention, reference is made to EPO Patent Nos. 277,003 and 277,004, the entire disclosures of which are incorporated herein by reference.

The bridged metallocene catalysts produced by the procedures of the present invention may be isospecific or syndiospecific, as discussed previously. The bridge configuration of the R" structural bridge is controlled by the terminal carbon substituents of the substituted fulvene. For example, where the fulvene reactant is 6, 6 dimethyl fulvene, as is preferred, the structural bridge will be a $C_3$ alkyl group (isopropyl). The use i of 6, 6 methyl ethyl fulvene will result in a $C_4$ structural bridge, and the use of 6, 6 diethyl fulvene as a reactant will result in a $C_5$ structural bridge. The bridge is preferably selected from the group consisting of alkyl radicals having 3-6 carbon atoms, more preferably, 3-5 carbon atoms. Examples of alkyl bridges include propyl, butyl and pentyl bridges, which may be substituted or unsubstituted. Me, preferably, is a Group 4 or 5 metal, and more preferably, a Group 4 metal, specifically, titanium, zirconium, or hafnium. Vanadium is the most suitable of the Group 5 metals. Q will usually be a methyl or ethyl group or chlorine.

Where the present invention is employed in the production of syndiospecific metallocene catalysts, the cyclopentadienyl and substituted fulvene reactants are preferably chosen so that the resulting syndiospecific catalysts exhibit bilateral symmetry of the metallocene ligands when viewed as planar projections of the cyclopentadienyl groups. By the term "bilateral symmetry" as used here, is meant the symmetry of the ligand as viewed through the axes of the substituted or unsubstituted $C_p$ groups. For example, the reaction of fluorene with 6, 6-dimethyl fulvene produces the isopropylidene (cyclopentadienyl-1-fluorenyl) ligand which exhibits such bilateral symmetry. However, the similar reaction carried out with a ring substituted fulvene such as a 3-alkyl, 6, 6-dimethyl fulvene, would result in a corresponding structure, but with the cyclopentadienyl group substituted at the three position, would not exhibit bilateral symmetry. The ligand with two identical substituents at the 3 and 4 positions on the cyclopentadienyl group would have bilateral symmetry.

Usually, in the catalysts prepared by the present invention, Me is titanium, zirconium, or hafnium; Q is, preferably, a methyl or halogen, more preferably chlorine; and k preferably, is 2 for neutral metallocenes, and 1 for cationic metallocenes, but may vary with the valence of the metal atom. Exemplary hydrocarbyl radicals include methyl, ethyl, propyl, isopropyl, butyl, isobutyl, amyl, isoamyl, hexyl, heptyl, octyl, nonyl, decyl, cetyl, phenyl, and the like. Other hydrocarbyl radicals include other alkyl, aryl, alkenyl, alkylaryl, or arylalkyl radicals. Further, $R_n$ and $R'_m$ may comprise hydrocarbyl radicals attached to a single carbon atom in the $C_p$ ring, as well as radicals that are bonded to two carbon atoms in the ring. Neutral metallocenes prepared in accordance with procedures of the present invention may be converted to the cationic state following procedures such as disclosed in the aforementioned European Patents Nos. 277,003 and 277,004, or more preferably, by reaction with triphenylcarbenium boronates, as described in the aforementioned U.S. application Ser. No. 419,046. Exemplary neutral syndiospecific metallocenes which may be prepared by the present invention are isobutylidene (cyclopentadienyl-1-fluorenyl), zirconium dimethyl isopentylidene (cyclopentadienyl-1-fluorenyl) zirconium dimethyl isopropylidene (indenyl) (cyclopentadienyl) zirconium dimethyl, isopropylidene (cyclopentadienyl-1-fluorenyl) zirconium dimethyl, and the corresponding dichlorides.

Examples of isospecific neutral metallocenes which can be prepared in accordance with the present invention include isopropylidene bis (cyclopentadienyl) zirconium dimethyl, isopropylidene bis (tetramethylcyclopentadienyl) zirconium dimethyl, and isopropylidene bis (2, 4 dimethylcyclopentadienyl) zirconium dimethyl, and the corresponding dichlorides. Other corresponding metallocenes, especially the corresponding hafnium and titanium metallocenes, can also be made in accordance with the present invention to produce syndiospecific or isospecific catalysts. Similarly, other metallocene dialkyls, for example, such as the zirconium diethyls and other dihalides, may also be made following the present invention, but, as a practical matter, the neutral metallocenes will be in the form of dimethyl or dichloride compounds, and the cationic metallocenes will usually be in the form of the chlorides.

As will be recognized from the foregoing description, the starting materials to be used in the practice of the present invention can readily be correlated with the desired metallocene product. For example, isopropylidene (cyclopentadienyl-1-fluorenyl) zirconium dimethyl can be prepared by deprotonation of fluorene, followed by the ligand forming reaction with 6,6 dimethyl fulvene, and the ligand ultimately reacted with zirconium dichloride to form the neutral metallocene. Similarly, an isospecific metallocene such as isopropylidene bis (cyclopentadienyl) zirconium dichloride can be prepared by deprotonation of cyclopentadiene, followed by reaction with 6, 6 dimethyl fulvene in the ligand-forming reaction. The bridged ligand can then be reacted with the appropriate transition metal compound, for example, titanium tetrachloride, to form the corresponding isopropyldiene bis (cyclopentadienyl) titanium dichloride.

The procedures involved in the present invention will be described in detail by reference to specific examples involving the production of isopropylidene (cyclopentadienyl fluroenyl) zirconium dichloride by the deprotonation of fluorene and reaction with 6,6 dimethyl fulvene. However, it will be recognized by those skilled in the art, that the following description is applicable to the production of other metallocenes by selection of the appropriate substituted or unsubstituted cyclopentadiene for the deprotonation reaction and the appropriate substituted fulvene.

The initial step in carrying out the invention involves the deprotonation of a substituted or unsubstituted cyclopentadiene, specifically, fluorene, in the example given, by the reaction of the fluorene in a polar solvent with a deprotonation agent. Any suitable deprotonizing agent may be employed in carrying out the invention, but preferred agents are alkali metal and alkaline earth metal deprotonizing agents. Such agents include methyl lithium, ethyl lithium, propyl lithium, butyl lithium, sodium hydroxide, potassium hydroxide, magnesium hydroxide and calcium hydroxide. The alkali metal deprotonizing agents such as those identified previously will normally be preferred over the alkaline earth metal agents. The preferred polar solvent for the fluorene during the deprotonization reaction is tetrahydrofuran (THF), although other aprotic polar solvents such as ethers and glycol ethers, for example, ethyl ether and 1,2 dimethoxyethane may also be used.

The deprotonizing agent is added slowly to the solution of the fluorene until the deprotonization reaction is carried to completion. By way of example, 44 grams (0.27 moles of fluorene) are added to 250 milliliters of tetrahydrofuran to form a 16.5 wt. %, 1.12 molar (m), solution of the fluorene in tetrahydrofuran. A solution of the preferred deprotonating agent (methyl lithium) is provided in the form of 1.4 molar (M) solution of methyl lithium in diethyl ether. The methyl lithium solution is added drop-wise with stirring to the fluorene solution, and the solution is stirred until gas (methane) evolution is carried to conclusion after a period of about three hours.

As the next step in the invention, the resulting anionic species (1-fluorenyl lithium in this example), is cooled to a temperature, preferably, in the sub-zero range, but substantially above the very low temperatures, typically, about $-80°$ C., used in previous synthesis procedures. Specifically, the anionic substituted or unsubstituted cyclopentadiene is cooled to a temperature no lower than $-30°$ C., and preferably, within the range of about $-10°$ to $-30°$ C.

At this point, the solution of substituted fulvene is added to the cooled solution. The substituted fulvene is employed in a concentration of less than 2 molar (m) in a polar solvent. The substituted fulvene is disubstituted on the terminal carbon atom, and may be substituted or unsubstituted on the cyclopentadienyl ring, as described previously. The preferred polar solvent for the substituted fulvene is tetrahydrofuran, although other solvents such as ethers and glycol ethers as noted previously may also be used. As a specific example of this step of the procedure, 30 grams (about 0.3 moles) of 6,6 dimethyl fulvene is added to 200 milliliters of tetrahydrofuran to provide a 1.6 molar solution.

The ligand-forming reaction is carried out by adding minor quantities of the fulvene solution to a major quantity of the cooled anionic substituted or unsubstituted cyclopentadiene. The fulvene solution is added slowly. For example, the 1.6 molar solution dimethyl fulvene in tetrahydrofuran may be added dropwise with stirring to the fluorenyl lithium solution over a period of about 3 to 12 hours. Thereafter, the reaction mixture is allowed to warm up, typically to room temperature, although the temperature may be increased to any value within the range of about 0° to 25° C. (room temperature).

At the conclusion of the ligand-forming reaction, the ligand may be recovered by any suitable technique. For example, in the reaction given above, after stirring the reaction mixture at ambient temperature for about 3 hours, the reaction mixture is treated with 100 milliliters of distilled water saturated with ammonium chloride, and then stirred for about 10 minutes. The organic layer is extracted with ether and dried over magnesium sulfate. After the ether is evaporated, the resulting yellow solvent is dissolved in chloroform and layered with an excess of methanol.

The bridged ligand, in the form of isopropylidiene (cyclopentadienyl flourenyl) lithium salt, may be converted to the metallocene by reaction with a transition metal compound of a formula MeQ$_k$, as described previously, and as set forth in the aforementioned U.S. parent Pat. No. 4,892,851. Preferably, the reaction is carried out with a titanium, zirconium, or hafnium compound, in which Q is a halogen, methyl or ethyl group. By way of example of the synthesis of the isopropylidiene (cyclopentadienyl fluorenyl) zirconium dichloride 5 grams of the isopropylidiene (cyclopentadienyl fluorenyl) lithium salt, prepared as described above, is placed under an argon atmosphere in a 250 milliliter flask. The flask is cooled to a temperature of about −10° C. Seventy-five milliliters of methylene chloride, at −10° C. is added to the flask, resulting in the immediate formation of a red solution. An equal molar amount of zirconium tetrachloride in 75 milliliters of methylene chloride, also at −10° C., is cannulated into the solution. The resulting mixture is warmed up to room temperature and the isopropyladiene (cyclopentadienyl fluorenyl) zirconium dichloride recovered by filtration to remove lithium followed by crystallization of the metallocene from the red solution.

Having described specific embodiments of the present invention, it will be understood that modifications thereof may be suggested to those skilled in the art, and it is intended to cover all such modifications as fall within the scope of the appended claims.

What is claimed is:

1 In a process for the preparation of a bridged metallocene catalyst, the steps comprising
(a) subjecting a hydrocarbyl substituted or unsubstituted cyclopentadiene to deprotonation in a polar solvent to produce a solution of an anionic form of said substituted or unsubstituted cyclopentadiene in said polar solvent;
(b) cooling the solution of said anionic substituted or unsubstituted cyclopentadiene resulting from step (a) to a temperature no lower than −30° C.;
(c) providing a solution of a substituted fulvene in a polar solvent in a concentration of less than 2 molar, said substituted fulvene being disubstituted on the terminal carbon atom and being substituted or unsubstituted on the cyclopentadienyl ring;
(d) adding minor quantities of the solution of step (c) to major quantities of the mixture of step (b) and increasing the temperature of the resulting mixture to a temperature within the range of 0° to 25° C. to produce a bridged dicyclopentadienyl ligand;
(e) recovering the bridged ligand from step (d); and
(f) contacting said bridged ligand with a metal compound of the formula MeQ$_k$ under reaction conditions sufficient to complex the bridged ligand with the metal compound to produce a bridged metallocene, wherein Me is a Group 4b, 5b, or 6b metal from the Periodic Table of Elements, and each Q is a halogen or a hydrocarbyl radical having 1–20 carbon atoms and $3 \leq k \leq 6$.

2. The process of claim 1, wherein Me is titanium, zirconium or hafnium, and k is 4.

3. The process of claim 2, wherein Q is a halogen or a methyl or ethyl group.

4. The process of claim 3, wherein the deprotonation of the substituted or unsubstituted cyclopentadiene in step (a) is carried out by reaction of an alkali metal or alkaline earth metal deprotonating agent.

5. The method of claim 4, wherein said deprotonizing agent is methyl lithium, ethyl lithium, propyl lithium, butyl lithium, sodium hydroxide, or potassium hydroxide.

6. The process of claim 4, wherein the cyclopentadienyl groups of the bridged cyclopentadienyl ligand are sterically different.

7. The process of claim 6, wherein the substituted or unsubstituted cyclopentadiene of step (a) is a substituted or unsubstituted fluorenyl group.

8. The process of claim 7, wherein said fluorenyl group is fluorene.

9. The method of claim 6, wherein said substituted or unsubstituted cyclopentadiene of step (a) is a substituted or unsubstituted indenyl group.

10. The process of claim 9, wherein said indenyl group is indene.

11. The process of claim 6, wherein the substituted fulvene of step (c) is a 6, 6-dialkyl substituted fulvene, in which each of the 6 dialkyl substituents is independently a methyl or an ethyl group.

12. The process of claim 11, wherein each of the 6,6 alkyl substituents is a methyl group.

13. The method of claim 12, wherein said substituted fulvene is a 6,6 dimethyl ring substituted fulvene.

14. The method of claim 12, wherein said substituted fulvene is a 6,6 dimethyl fulvene.

15. In a process for the preparation of a bridged metallocene catalyst, the steps comprising
(a) reacting an alkali metal or alkaline earth metal deprotonizing agent with a hydrocarbyl substituted or unsubstituted cyclopentadiene in a polar solvent to deprotonate said cyclopentadiene and form a solution of an alkali metal or alkaline earth metal salt of said substituted or unsubstituted cyclopentadiene in said polar solvent;
(b) cooling the solution of said deprotonized substituted or unsubstituted cyclopentadiene resulting from step (a) to a temperature no less than about −30° C.;

(c) providing a solution of a substituted fulvene in a polar solvent in a concentration of less than 2 molar, said substituted fulvene being on the terminal carbon atom and being substituted or unsubstituted on the cyclopentadienyl ring;

(d) adding minor quantities of the solution of step (c) to a major quantity of the mixture of step (b) and increasing the temperature of the resulting mixture to a temperature within the range of about 0° to 25° C. to produce a bridged dicyclopentadienyl ligand;

(e) recovering the bridged ligand from step (d); and (f) contacting said bridged ligand with a metal compound of the formula $MeQ_k$ under reaction conditions sufficient to complex the bridged ligand with the metal compound to produce a bridged metallocene, wherein Me is a Group 4b, 5b or 6b metal from the Periodic Table of Elements, each Q is a hydrocarbyl radical having 1–20 carbon atoms or is a halogen and $3 \leq k \leq 6$.

16. The process of claim 15, wherein Me is titanium, zirconium, or hafnium, and k is 4.

17. The process of claim 16, wherein Q is a halogen or a methyl or ethyl group.

18. The process of claim 16, wherein MeQk is titanium, zirconium, or hafnium tetrachloride.

19. The process of claim 18, wherein said deprotonizing agent is methyl lithium, ethyl lithium, potassium hydroxide, or sodium hydroxide.

20. The process of claim 19, wherein said deprotonizing agent is methyl lithium or ethyl lithium.

21. The process of claim 19, wherein the cyclopentadienyl groups of the bridged cyclopentadienyl ligand are sterically different.

22. The process of claim 21, wherein the substituted or unsubstituted cyclopentadiene of step (a) is a substituted or unsubstituted fluorenyl group.

23. The process of claim 22, wherein said fluorenyl group is fluorene.

24. The process of claim 22, wherein the substituted fulvene of step (c) is a 6, 6-dialkyl substituted fulvene in which each of the 6 dialkyl substituents is independently a methyl or an ethyl group.

25. The process of claim 24, wherein each of the 6,6 alkyl substituents is a methyl group.

26. The method of claim 25, wherein said substituted fulvene is 6,6 dimethyl fulvene.

27. In a process for the preparation of a bridged metallocene catalyst, the steps comprising (a) incorporating a solution of methyl lithium in diethyl ether with a solution of a substituted or unsubstituted cyclopentadiene in tetrahydrofuran by adding the methyl lithium solution in small amounts to a larger quantity of the solution of substituted or unsubstituted cyclopentadiene in tetrahydrofuran;

(b) cooling the resulting mixture from step (a) to a temperature within the range of about −10° to −30° C.;

(c) providing a solution of 6,6 dialkyl fulvene in tetrahydrofuran in a concentration of less than 2 molal;

(d) adding minor quantities of the solution of step (c) to a major quantity of the mixture of step (b), and increasing the temperature of the resulting mixture to a temperature within the range of 0° to 25° C. to produce a bridged dicyclopentadienyl ligand;

(e) recovering the bridged ligand from step (d); and (f) contacting said bridged ligand with a metal compound of the formula $MeQ_k$, under reaction conditions sufficient to complex the bridged ligand with the metal compound to produce a bridged metallocene, wherein Me is a Group 4b, 5b, or 6b metal from the Periodic Table of Elements, and each Q is a hydrocarbyl radical having 1–20 carbon atoms or is a halogen and $3 \leq k \leq 6$.

28. The process of claim 27, wherein the cyclopentadienyl groups of the bridged cyclopentadienyl ligand are sterically different.

29. The process of claim 28, wherein the substituted or unsubstituted cyclopentadienyl of step (a) is a substituted or unsubstituted fluorenyl group.

30. The process of claim 29, wherein said fluorenyl group is fluorene.

31. The method of claim 30, wherein said 6,6 dialkyl fulvene is 6,6 dimethyl fulvene.

32. The process of claim 1, wherein each of the cyclopentadienyl groups of the bridged dicyclopentadienyl ligand is characterized by the formula CpRn wherein each Cp represents a cyclopentadienyl ring, each R is independently a hydrocarbyl radical having from 1–20 carbon atoms and n varies from 0 to 4.

33. The process of claim 1, wherein the cyclopentadienyl groups of the bridges dicyclopentadienyl ligand are characterized by the formulas CpRn and CpR'm, wherein Cp represents a cyclopentadienyl ring; each R and R' is independently a hydrocarbyl radical having from 1 to 20 carbon atoms, n varies from 0 to 4, m varies from 1 to 4, and R and R' are selected such that CpR'm is a sterically different cyclopentadienyl group than CpRn.

* * * * *